United States Patent [19]

Pennetta

[11] Patent Number: 5,626,472
[45] Date of Patent: May 6, 1997

[54] SHOWER MOUNTED DENTAL HYGIENE DISPENSER

[76] Inventor: Richard J. Pennetta, 6 Stonegate, Upper Saddle River, N.J. 07458

[21] Appl. No.: 452,118

[22] Filed: May 26, 1995

[51] Int. Cl.$^6$ .................................................. A61C 17/00
[52] U.S. Cl. .............................................. 433/80; 601/165
[58] Field of Search .................................. 601/162, 165; 433/80, 88

[56] References Cited

U.S. PATENT DOCUMENTS

| | | | |
|---|---|---|---|
| 1,209,599 | 12/1916 | Le Fevre | 433/80 |
| 2,208,031 | 7/1940 | Hooper | 128/229 |
| 3,225,759 | 12/1965 | Drapen et al. | 601/165 |
| 3,545,435 | 12/1970 | Hollander et al. | 601/162 |
| 3,568,667 | 3/1971 | Krieger et al. | 601/165 |
| 3,820,532 | 6/1974 | Eberhardt et al. | 601/165 |
| 3,870,045 | 3/1975 | Vaughan | 128/229 |
| 4,043,337 | 8/1977 | Baugher | 128/229 |
| 4,265,229 | 5/1981 | Rice et al. | |
| 4,564,005 | 1/1986 | Marchand et al. | |
| 4,903,687 | 2/1990 | Lih-Sheng | 601/165 |
| 4,942,870 | 7/1990 | Damien | 601/165 |
| 4,979,504 | 12/1990 | Mills | 601/165 |
| 4,991,569 | 2/1991 | Martin | 601/165 |
| 5,220,914 | 6/1993 | Thompson | |

Primary Examiner—Paul J. Hirsch
Attorney, Agent, or Firm—Bill D. McCarthy; Randall K. McCarthy; Phillip L. Free, Jr.

[57] ABSTRACT

A shower mounted hygiene dispenser for discharging a stream of water or a mixture of water and hygienic fluid for oral irrigation, the dispenser having a conduit housing connectable to a domestic water source. A dispenser assembly contains a collapsible bag of hygienic fluid which selectively discharges the hygienic fluid into the conduit housing in response to differential pressure exerted upon the bag to provide a mixture of water and hygienic fluid. An applicator assembly comprising a hose and a nozzle assembly delivers either pressurized water or a mixture of water and hygienic fluid for personal hygiene usage, such as for oral irrigation. A pressure regulating valve regulates the water pressure through the conduit housing.

19 Claims, 3 Drawing Sheets

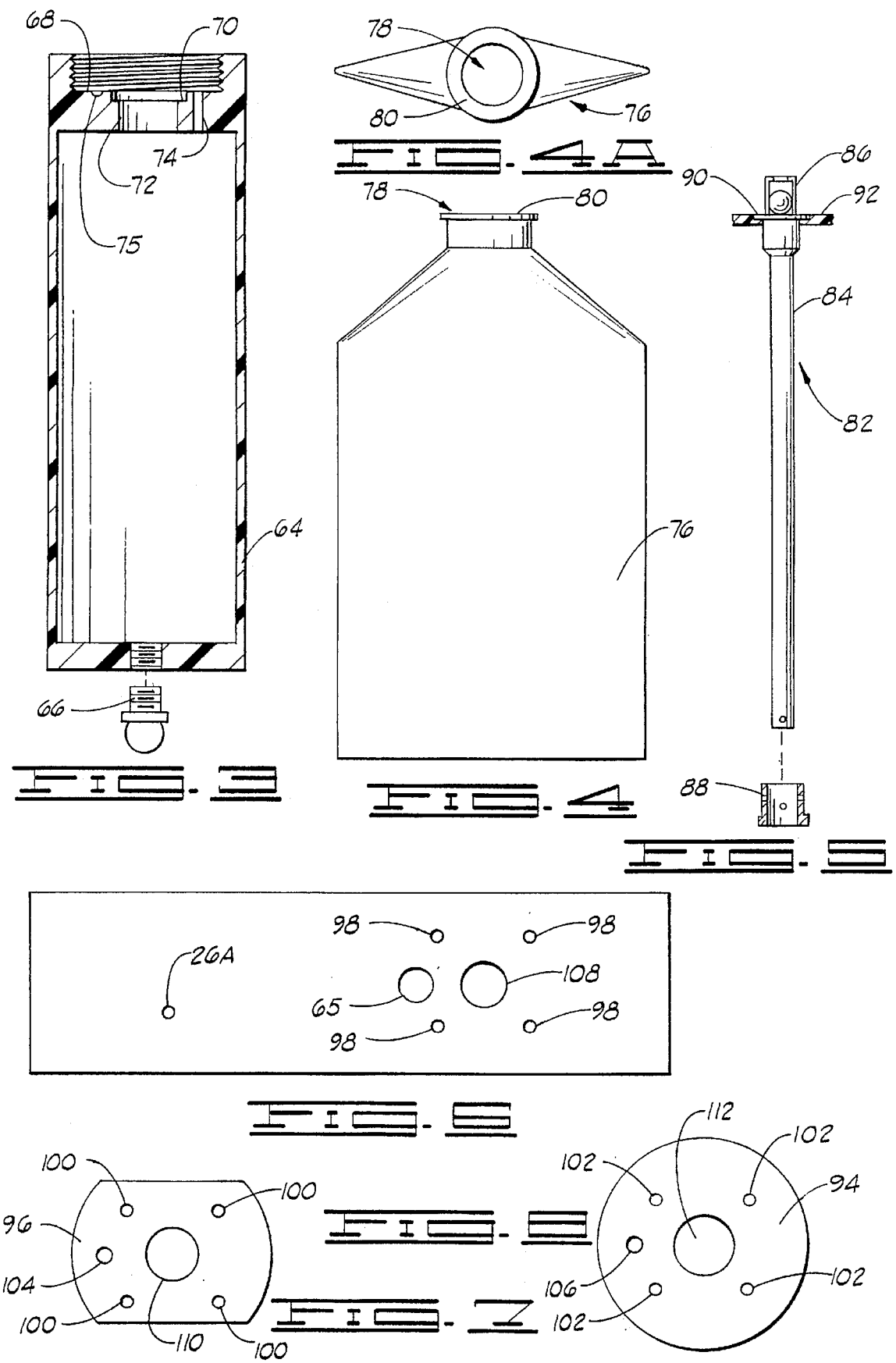

SHOWER MOUNTED DENTAL HYGIENE DISPENSER

BACKGROUND OF THE INVENTION

1. Field of the Invention

The present invention relates generally to personal hygiene and more particularly, but not by way of limitation, to a shower mounted dental hygiene dispenser for dispensing a hygienic fluid such as a mouthwash to aid in dental hygiene.

2. Brief Description of the Prior Art

As is well known, a regular and effective dental hygiene regimen is an important factor in combating gum and tooth disease and decreasing dental health problems. In recent times, advancements in the art of dental hygiene beyond conventional methods of brushing and flossing have included devices that discharge a stream of pressurized water. This discharged water enables a user to irrigate the mouth, eject food particles from between teeth, and clean above and below the gum line.

One well known variety of such devices comprises a unit placed on a counter surface next to a sink with a reservoir that is filled with water or with a mixture of water and hygienic fluid. Such devices generally employ an electrical pump to direct a stream of water from the reservoir to an applicator nozzle by way of a hose member. Although such devices have been commercially popular, these devices have not been without attendant problems such as the annoying noise and vibration of the pump, a propensity to create a mess on the counter from the discharged water, and the potential risk of electrical shock.

Advancements in the art to address such problems have included devices exemplified by references such as U.S. Pat. No. 4,991,569, issued to Martin and U.S. Pat. No. 4,903,687, issued to Lih-Sheng.

These and other related references teach the use of an applicator nozzle attached to a water source, such as a sink or in a shower or tub, by way of a hose and an attachment member for directing a stream of water from the water source to the applicator nozzle, thereby enabling the user to effectively irrigate the mouth. Such devices eliminate the annoyance and potential hazard from the use of an electrical pump, relying instead upon the pressure of the water from the water source to propel the water through the applicator nozzle. In addition, insofar as those devices used in a shower or tub are concerned, these devices eliminate the mess associated with a counter-top unit by attempting to restrict the discharge to the confines of the shower or tub.

Additionally, devices have also been developed that provide a pressurized stream of water from a water source mixed with a hygienic fluid, such as disclosed by U.S. Pat. No. 4,564,005, issued to Marchand et al. and U.S. Pat. No. 5,220,914, issued to Thompson. These and other related references teach the use of either solid pellets that dissolve in a stream of water to provide a mixture of water and hygienic fluid or the use of a liquid that is emitted from a reservoir and mixed with the flow of water to provide the mixture.

Nevertheless, advancements in the art are still necessary to address problems related to the control of the mixing and the discharge of the water or the water and mixture of hygienic fluid. Pressurized water from a domestic water source is typically presented to the devices described hereinabove and regulated by the selective opening of manual valves which often do not enable the user to properly set the appropriate pressure of the water or mixture. It is known that a pressure of from 20 to 25 psig (pounds per square inch gauge) is recommended for safe and effective dental cleaning, and that excessive pressures may cause discomfort or even injury to gum tissues. Typical domestic water systems may provide water pressures of 75 to 100 psig, and so this pressure must be effectively reduced and controlled. Contrawise, some domestic water systems, especially well systems, may also experience fluctuations in water pressure during use of a device, further compounding the problem of accurately controlling the pressure of the discharged water or mixture.

Further, it is desirable to provide a dispenser with improved hygienic liquid discharge characteristics. This would provide effective and uniform rates of discharge so that the flow of hygienic liquid and the resulting mixture concentration is precisely controlled and that all the available hygienic liquid in a dispenser is effectively discharged before the need to replenish the source arises. It is to such problems with the prior art that the present invention is directed.

SUMMARY OF THE INVENTION

The present invention provides a hygienic fluid dispenser that delivers pressure regulated water or a mixture of water and a hygienic fluid to a user to allow irrigation of a body cavity. In a preferred embodiment, the dispenser is mounted in the shower and used for dental hygiene. The dispenser enables the user to clean the gum line, clean below the gum line, and flush out particles trapped between the teeth so as to remove bacteria, reduce bleeding and inflammation of gums and prevent build up of plaque associated with gingivitis.

The invention comprises a conduit housing having first, second and third openings, the first opening connectable to a domestic water source and serving as an inlet to admit a flow of water through the housing. The second opening serves as a dispenser conduit for receiving a flow of hygienic liquid, such as mouthwash, from a dispenser assembly connected to the conduit housing. The dispenser assembly contains a collapsible bag of hygienic fluid and a portion of the water flowing through the conduit housing is routed so as to enter the dispenser assembly and occupy a volume surrounding the bag so that the water exerts a pressure upon the bag. The aforementioned second opening in the conduit housing contains a flow control valve that selectively allows passage of the hygienic fluid from the bag into the conduit housing. The hygienic fluid that passes through the second opening mixes with the flow of water and provides a mixture of water and hygienic fluid to the third opening in the conduit housing, which is a dispenser outlet connected to an applicator means, which comprises a hose and a nozzle assembly containing a nozzle valve for regulating the flow of the mixture through the nozzle. The flow control valve can be closed to obtain a flow of pure water through the nozzle or the user can variably adjust the flow of the hygienic fluid into the water stream to a desired mixture concentration.

Additionally, the invention comprises the use of a pressure regulating valve to provide the water or mixture at a safe and desired pressure range and compensate for water source pressure variations that are characteristic in well water systems. A pressure gauge can also be employed to provide an analog reading of the pressure of the water or mixture supplied to the nozzle. Additional features include an anti-siphon valve to prevent a back flow of water from the conduit housing into the water source and a by-pass valve useful for purging water from the dispenser as shower valves in the shower are adjusted.

An object of the present invention is to provide a hygienic fluid dispenser that delivers pressure regulated water or a mixture of water and a hygienic fluid to a user to allow irrigation of a body cavity.

Another object of the present invention is to provide a shower mounted dental hygiene dispenser to allow a user to irrigate the mouth with water or a mixture of water and mouthwash.

Still another object of the present invention is to provide a hygienic dispenser with an unlimited water source, eliminating the need to fill a water reservoir.

Yet another object of the present invention is to provide a hygienic dispenser that has no electrical components and does not provide annoying motor pump noises during use.

Still yet another object of the present invention is to provide a hygienic dispenser with a collapsible bag for containing and discharging hygienic fluid at a controllable rate.

Other objects, features and advantages of the present invention will become apparent from the following detailed description when read in conjunction with the drawings and appended claims.

BRIEF DESCRIPTION OF THE DRAWINGS

FIG. 3 provides a cross-sectional view of a dispenser assembly of the dispenser of FIG. 2.

FIG. 4 provides a cross-sectional view of a dispenser bag of the dispenser of FIG. 2. FIG. 4A provides a top-view of the bag of FIG. 4.

FIG. 5 provides an exploded representation of a dip tube assembly of the dispenser of FIG. 2.

FIG. 6 provides a bottom view representation of a conduit housing of the dispenser of FIG. 2.

FIG. 7 provides a bottom view representation of a dispenser gasket of the dispenser of FIG. 2.

FIG. 8 provides a bottom view representation of a dispenser hub of the dispenser of FIG. 2.

FIG. 9 provides a cross-sectional representation of a nozzle assembly of the dispenser of FIG. 1.

DESCRIPTION

Figure 1:
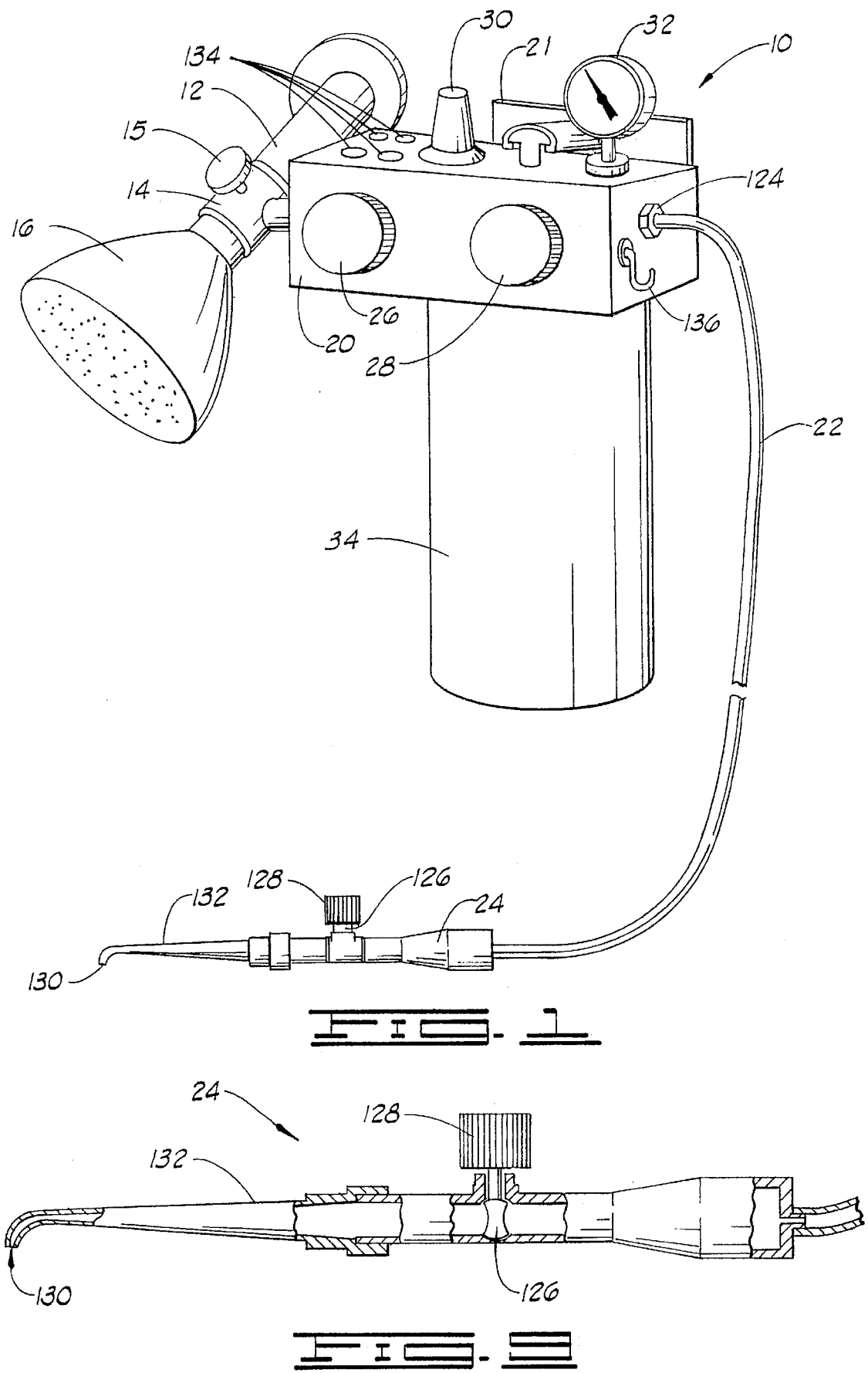
FIG. 1 provides a perspective view of the preferred embodiment of the present invention, which is a shower mounted dental hygiene dispenser.

Referring now to the drawings in general, and more particularly to FIG. 1, shown therein is a perspective view of the preferred embodiment of the present invention which is a shower mounted dental hygiene dispenser, identified generally in the figure as item number 10. As can be seen in FIG. 1, the dispenser 10 is connected to a shower head assembly 12 by way of a conventional two way diverter 14 with a valve 15 which selectively provides a main conduit for water to pass from a domestic water source (not shown) to a shower head 16 and provides a secondary conduit for water from the source to pass to the dispenser 10.

FIG. 1 shows the dispenser 10 having a conduit housing 20 which is a substantially rectangularly shaped member that forms the main body of the dispenser 10 and is attached by way of a bracket assembly 21 to the wall of the shower (not shown) from which the shower head assembly 12 protrudes. Generally, the housing 20 provides a path for water to flow from the water source to an applicator assembly made of a flexible hose 22 attached to the right side of the housing 20 and a nozzle assembly 24, which delivers a stream of pressurized water or a mixture of water and a hygienic fluid to the user for irrigation of the mouth. The hose 22 is about four feet long, providing sufficient length to enable the user to comfortably and efficiently manipulate the nozzle assembly 24.

Referring again to the housing 20, FIG. 1 shows it to contain several components for which the construction and operation will be more fully described below, but the outwardly facing side of the housing 20 can be immediately seen to hold two user accessible knobs, the left-most one being the handle for a depressible by-pass valve 26 which enables the user to open a port (not shown in FIG. 1) on the bottom of the housing 20 to temporarily purge water from the dispenser 10 while the temperature of the water from the shower is adjusted by the user. The other knob is a handle for a flow control valve 28 which, as will also be more fully described, regulates the flow of the hygienic fluid such as a mouthwash into the flow of water through the conduit so as to provide the aforementioned mixture of water and hygienic fluid at a concentration level selected by the user.

The top side of the housing 20 is shown to hold a rotary knob which is a handle for a pressure regulating valve 30 which reduces and regulates the pressure of the water or mixture to a safe and desired pressure level. By turning the knob of the regulating valve 30, the user may increase or decrease the pressure as desired. Next to the housing 20 and on the other side of the bracket assembly 21 is shown a pressure gauge 32, which provides an analog readout of the pressure of the water and mixture provided to the nozzle assembly 24. As is generally known by those of skill in the art, a water pressure of between 20 and 25 pounds per square inch gauge (psig) is recommended for safe and effective oral cleaning.

Finally, although the bottom side of the housing 20 is not visible in FIG. 1, shown attached to the bottom of the housing 20 is a dispenser assembly 34 which houses and dispenses the hygienic fluid in a manner in accordance with the present invention. The construction and operation of the dispenser assembly 34 will be more particularly described below.

Figure 2:
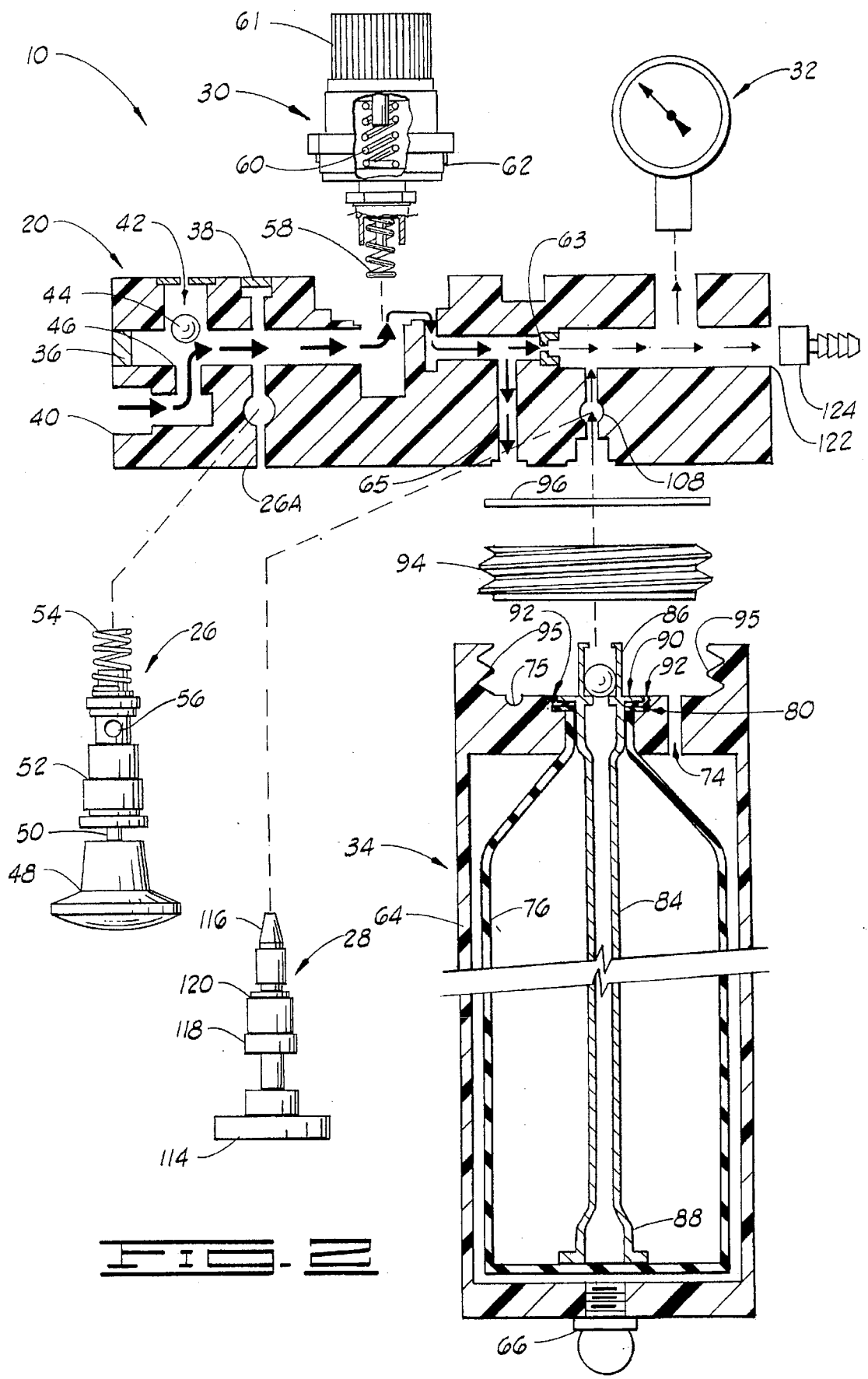
FIG. 2 provides an exploded, cross-sectional representation of the dispenser of FIG. 1.

Referring now to FIG. 2, shown therein is an exploded, cross sectional view of the main body of the dispenser 10, including a cross sectional view of the conduit housing 20 constructed in accordance with the present invention. To simplify the discussion, the relevant components that normally reside within or are connected to the conduit housing 20 are shown detached from the conduit in an exploded fashion, with dashed lines indicating the location where these components normally reside. In addition, the hose 22 and the nozzle assembly 24 (shown in FIG. 1) are omitted from this drawing.

The conduit housing 20 is fabricated from a block of a suitable material, such as PVC, which may be machined using conventional methods in such a manner as to provide the various ports and interior channels shown. As is known by those of skill in the art, when machining a block of material it is sometimes necessary to drill fabrication ports to cut particular interior channels that cannot otherwise be accessed through functional ports. Such fabrication ports are subsequently sealed and do not generally serve any functional purpose after the part has been fabricated. It is contemplated that in one preferred embodiment of the present invention the housing 20 would be machined from PVC and include sealed fabrication ports, such as those shown as items 36 and 38. However, a preferred alternative method for fabricating the housing 20 in a high volume production environment would be to use injection molding using suitably tooled molds. If the housing 20 was injection molded, of course, no such fabrication ports would be necessary. It is contemplated that injection molding, beyond the obvious per-unit cost savings, would also provide the benefit of fabricating housings 20 in almost any desired color simply by altering the color of the injected plastic.

The functional ports of the conduit housing 20 include a water source inlet 40 that fluidly connects the housing 20 to the two way diverter 14 (shown in FIG. 1) by way of a conventional threaded screw arrangement (the details of which are well known and as such are not particularly shown). During operation of the dispenser 10, a flow of pressurized water from the domestic water source passes through the inlet 40 and into the conduit housing 20, taking the paths indicated by arrows. As will be more fully explained below, the relative size of the arrows indicates the relative pressure of the water as it flows through the housing 20.

The flow of water through the inlet 40 first encounters an anti-siphon valve 42 which includes a stainless steel ball 44 that is lifted off of a normally closed (N/C) neoprene or teflon seat 46 by the flow of pressurized water. The anti-siphon valve 42 serves as a one-way check valve to allow water to pass into the housing 20, but to prevent water from siphoning back out of the housing 20 when water pressure is not present at the inlet 40. The anti-siphon valve 42 vents to the atmosphere in a conventional manner as shown.

The flow of water next passes to the by-pass valve 26 that is installed in the conduit housing 20 in a by-pass valve channel as shown. During normal operation of the dispenser 10 the water flows past the N/C by-pass valve 26, but a path through a by-pass port 26A is established when the by-pass valve 26 is depressed by the user, allowing the flow of water to be diverted out the bottom of the housing 20 through the by-pass port 26A.

The purpose of the by-pass valve 26 is to allow the user to easily obtain a desired water temperature for use with the dispenser 10 without utilizing or wasting any mouthwash solution. It is contemplated that a user may wish to use the dispenser 10 to irrigate his mouth after having taken a hot shower, but he would first want to adjust the water to a cooler temperature to avoid any discomfort to the gums caused by the application of the hot water used during the shower. By depressing the by-pass valve 26 for a few seconds while adjusting the shower water valves (not shown), the desired water temperature can be obtained and immediately used; without such a by-pass valve, a user would have to discharge water out the nozzle assembly 24 (as shown in FIG. 1) for several minutes to purge the system of the water at the undesirable hot temperature before using the dispenser 10.

Likewise, in situations where the shower was not just previously in use, the user can temporarily depress the by-pass valve 26 to prevent the dispenser 10 from filling up with the undesirable cold water that characteristically flows from most domestic shower systems when such systems are initially turned on.

Referring again to FIG. 2 the by-pass valve 26 is shown to be a conventional, spring loaded valve with a handle 48, a valve stem 50, a valve body 52, and a spring 54 fabricated and connected as shown. When the valve handle 48 is depressed into the channel, the entire assembly moves inwardly, compressing the spring 54 against a back wall of the channel (not particularly shown) which aligns a hole 56 in the valve body 52 with the by-pass port 26A so that, as previously described, water from the inlet 40 is discharged out the bottom of the housing 20.

Continuing with an examination of the flow of water through the housing 20, the flow is shown to continue past the by-pass valve 26 and to next encounter the pressure regulating valve 30. As is known, the pressure regulating valve 30 regulates downstream water pressure by employing a lower spring 58 and an adjustable upper spring 60 that are in compression on each side of a diaphragm assembly 62. Water thus selectively passes through the pressure regulating valve 30 in response to the water pressure on each side of the diaphragm assembly 62.

More particularly, pressure is exerted on the bottom of the diaphragm assembly 62 from the combined force of the lower spring 58 and the pressure from the flow of water from the inlet 40. At the same time, pressure is exerted on the top of the diaphragm assembly 62 from the combined force of the adjustable upper spring 60 and the pressure of water that has passed through the diaphragm assembly 62. When the pressure regulating valve 30 is first presented with pressurized water at the bottom of the pressure regulating valve 30, water flows up through the diaphragm assembly 62 until such time that the pressure from the water that has passed through and is subsequently on the top of the diaphragm assembly 62 and exerts a back pressure on the diaphragm assembly 62. When this back pressure reaches a particular threshold level, the diaphragm assembly 62 closes. The diaphragm assembly 62 reopens and admits additional water as the water pressure from the water on top decreases as it flows downstream (and is discharged through the nozzle assembly 24, as shown in FIG. 1). In this manner, the pressure regulating valve 30 maintains a relatively constant pressure downstream and allows for improved control of the upstream pressure from the water source, which may typically be 75 to 100 psig. The pressure regulating valve 30 also compensates for variations in water pressure that can be observed in domestic well systems.

The downstream pressure may be adjusted by changing the preload on the adjustable upper spring 60 by turning a user accessible handle 61 on the pressure regulating valve 30. As previously discussed hereinabove, the user may rotate the handle 61 to select a desired pressure of the discharged water or mixture through the nozzle assembly 24. This adjustability allows the user to increase the pressure to a relatively larger value, such as 25 psi, which would be useful in ejecting food particles from between the teeth and gums. In addition, the pressure may be reduced to a relatively low value, such as 15 psig, which may be preferred by some users such as children. The pressure regulating valve 30 is available commercially such as model R362 manufactured by Arrow Pneumatics, Inc.

Referring again to FIG. 2, it can be seen that the flow of water exits the pressure regulating valve 30 and flows through a nozzle feed orifice port 63 and a dispenser assembly inlet port 65. The inlet port 65 provides the flow of water to the dispenser assembly 34 in a manner to be described below. To understand the operation of the dispenser assembly 34, however, it is first necessary to provide a detailed description of the components and construction therein.

The dispenser assembly 34 is shown in FIG. 2 to comprise a cylindrical dispenser housing 64, preferably made of acrylic. FIG. 3 provides an unobstructed cross-sectional view of the dispenser housing 64, and it can be seen that the dispenser housing 64 may be fabricated from a hollow cylinder of acrylic or other suitable material and capped off at both ends with fabricated (preferably machined) pieces of acrylic glued or otherwise affixed to the cylinder to provide an interior volume within the dispenser housing 64. In the preferred embodiment, the dispenser housing 64 is fabricated from cast acrylic tubing with a 3-inch outer diameter and ⅛-inch wall thickness, and the completed dispenser housing 64 has an overall length of about 9 inches. The bottom of the dispenser housing 64 has a ½ inch diameter threaded hole for accepting a threaded plastic drain plug 66, as shown in FIG. 2 and FIG. 3, which may be removed as described below to drain water from the dispenser housing 64. As can be seen in FIG. 3, the top of the dispenser housing 64 has a first circular, recessed shelf 68 and a second circular, recessed shelf 70 within and below the first shelf 68, so that the shelves "step down" into the dispenser housing 64. The top of the dispenser housing 64 also comprises a central opening 72 through the first and second shelves 68, 70 that allows access to the interior volume of the dispenser housing 64. A secondary opening 74 also allows access to the interior volume, but the secondary opening 74 exists in the first shelf 68 only and not the second shelf 70. A semi-circular shaped channel 75 is also cut in the first shelf 68 and runs in a path completely surrounding the second shelf 70, aligned so as to communicate with the secondary opening 74. For clarity, it should be understood that the channel 75 has a semi-circular shape in regards to its cross-sectional depth, but it is circular in shape in regards to the path it takes around the second shelf 70. The purpose of these various elements will become clear as additional elements associated with the dispenser assembly 34 are further identified and described.

The dispenser assembly 34 further comprises a collapsible dispenser bag 76 for retaining and dispensing a hygienic fluid, such as the mouthwash previously discussed. The dispenser bag 76 is located within the interior volume of the dispenser housing 64 and, as shown more fully in FIGS. 4 and 4A, is made of polyethylene film, with ethylene vinyl acetate (EVA) content and with a wall thickness of about 0.004 inches. The bag material should be impervious to the effects of alcohols and other chemicals commonly contained in the hygienic fluids used with the dispenser 10.

As will be apparent to those of skill in the art, for clarity of illustration the wall thickness of the dispenser bag 76 in FIG. 2 is shown in exaggerated dimension and no folds in the bag are shown, although such folds may exist when the dispenser bag 76 is inserted into the dispenser housing 64. The dispenser bag 76, also shown in FIG. 4, has an opening 78 with a gasket 80 made of polyethylene with EVA content approximately 1/16 inch thick attached thereto. FIG. 4A provides a top plan view of the gasket 80.

As shown in FIG. 5, the dispenser assembly 34 also comprises a dip tube assembly 82 which is a long, hollow tube 84 having a simple ball check valve 86 affixed at the top of the tube 84 and a diffuser 88 affixed to the bottom of the tube 84. The diffuser 88 has holes that align and communicate with holes in the tube 84 as shown. The top of the tube assembly 82 has a shelf 90 that protrudes as a ring around the tube 84 and fits into a circular gasket 92, which has essentially the same diameter as the second shelf 70 in the dispenser housing 64.

The dispenser bag 76 is inserted into the interior volume of the dispenser housing 64 so that the gasket 80 which is attached to the opening of the dispenser bag 76 rests upon the second shelf 70 in the top of the dispenser housing 64. The gasket 80 thus holds the dispenser bag 76 open and prevents the dispenser bag 76 from completely entering the interior of the dispenser housing 64. The dip tube assembly 82 is inserted into the bag so that the gasket 92 compresses the gasket 80 in the opening 78 of the dispenser bag 76 and essentially fills the space provided by the second shelf 70 in the dispenser housing 64. The gasket 92 thus provides a water tight seal between the dispenser housing 64, the tube assembly 82, and the dispenser bag 76.

Observing the dispenser housing 64 in FIG. 2, it can be seen that the top opening of the dispenser housing 64 also has threaded sides 95 which enable the dispenser housing 64 to be screwed to a dispenser hub 94 which, along with a dispenser hub gasket 96 (more particularly shown in FIG. 7), is affixed to the bottom of the conduit housing 20.

FIG. 6 provides a bottom view of the housing 20 and shows mounting holes 98 through which hardware screws (not shown) mount the gasket 96 (through corresponding gasket mounting holes 100, as shown in FIG. 7) and the hub 94 (through corresponding hub mounting holes 102, as shown in FIG. 8) to the housing 20. Of course, if the housing 20 was fabricated by way of the aforementioned injection molding process, the hub 94 could be formed as an integral part of the housing 20, and in such a case the gasket 96, the holes 100 and 102, and the hardware would then be unnecessary.

FIG. 7 shows the gasket 96 as containing a secondary opening 104 which is aligned with the dispenser assembly inlet port 65. FIG. 8 further shows that the hub 94 contains a hub secondary opening 106 that aligns with both the gasket secondary opening 104 and the dispenser assembly inlet port 65. Thus, water may freely pass out of the dispenser assembly inlet port 65 and through both the gasket 96 and the hub 94 through the openings 104 and 106.

Returning now to FIG. 2, the dispenser assembly 34, when screwed to the housing 20 by way of the hub 94, provides a path for a flow of water to pass to the dispenser housing 64 and occupy the volume of space surrounding the dispenser bag 76. Such a flow of water passes through the dispenser assembly inlet port 65, through the gasket 96 and hub 94, and enters the channel 75 in the top of the housing 20. The water fills and follows the channel 75 until reaching the housing secondary opening 74, after which it flows through the secondary opening 74 and fills the volume surrounding the dispenser bag 76. With the bag filled with mouthwash, the water surrounding the dispenser bag 76 will exert an inward pressure upon the sides or wall of the collapsible dispenser bag 76 and the mouthwash, provided no opening is made so that mouthwash may flow from the dispenser bag 76, will exert an outward pressure of equal magnitude upon the wall of the dispenser bag 76 from inside the dispenser bag 76.

Returning now to the description of the flow of water through the conduit housing 20 as shown in FIG. 2, the flow of water downstream past the pressure regulator valve 30 was described as splitting into two paths, with one path through the nozzle feed orifice port 63 and the other path through the dispenser assembly inlet port 65. It should be now readily understood that the water passing through the inlet port 65 serves to pressurize the dispenser assembly 34 by providing a volume of pressurized water surrounding the dispenser bag 76 at a pressure essentially that determined by the pressure regulating valve 30.

The water passing through the orifice port 63, however, provides the water to be discharged through the nozzle assembly 24, as shown in FIG. 1. The orifice port 63, which is a conventional brass orifice, provides a small pressure drop of perhaps 1 to 2 psig as the water passes through the orifice port 63. This reduced water pressure is indicated by the smallest of the three sizes of arrows shown in FIG. 2 representing the flow of water through the housing 20. The purpose for this small pressure drop will be apparent below.

The housing 20 contains a discharge conduit 108 (as shown in FIGS. 2 and 6) that communicates with the dispenser assembly 34 and aligns with the central opening 72 in the dispenser housing 64, as shown in FIG. 3. The hub gasket 96 has a gasket central opening 110 that aligns with the discharge conduit 108, as can be seen in FIG. 7, and the hub 94 likewise has a hub central opening 112, as shown in FIG. 8, that also aligns with the discharge conduit 108 and accepts the top of the ball check valve 86 of the dip tube assembly 82. Thus, a fluid path is established from the dispenser bag 76, through the dip tube assembly 82, the central openings 110 and 112 in the gasket and hub respectively, and finally to the discharge conduit 108, to allow the passage of mouthwash into the housing 20.

The discharge conduit 108 also contains the flow control valve 28, described hereinabove with reference to FIG. 1, and the flow control valve 28 regulates the flow of mouthwash from the dispenser bag 76 into the conduit housing 20. The flow control valve 28 is a conventional needle rotary valve that may be completely closed, so that no mouthwash flows through the valve, or may be opened gradually to allow a continuously increasing amount of mouthwash through the valve. The flow control valve 28 in FIG. 2 is shown to comprise a handle 114 attached to a valve stem 116 that rotates through a threaded packing nut assembly 118 secured to the housing 20. A teflon valve sleeve 120 is also shown to provide a watertight seal to prevent leakage.

As previously described, during operation with the flow control valve 28 closed, pressure will be exerted upon the dispenser bag 76 by the surrounding water inside the dispenser housing 64. If, by way of example, the pressure regulating valve 30 is set so as to provide a flow of water at about 25 psi downstream, the pressure both inside and outside the dispenser bag 76 will be about 25 psi, and water passing beyond the orifice port 63 will have a pressure of about 23 psi.

However, once the flow control valve 28 is opened, the pressure inside the dispenser bag 76 will drop to a level substantially equal to that of the flow of water beyond the orifice port 63, namely about 23 psi, whereas the pressure outside the dispenser bag 76 will remain at about 25 psi. This differential pressure will cause mouthwash to flow up through the discharge conduit 108 and mix with the water passing beyond the orifice port 63, generating a mixture of water and mouthwash to be discharged through the nozzle assembly 24. The volume of mouthwash, and hence the concentration of mouthwash in the mixture, will be determined by the extent that the flow control valve 28 is opened; opening the flow control valve 28 to a greater extent allows a greater flow of mouthwash through the discharge conduit 108 and making a "richer" mixture with a greater concentration of mouthwash.

The flow of water, or the mixture of water and mouthwash when the flow control valve 28 is open, is shown in FIG. 2 to proceed beyond the orifice port 63 and pressurize the conventional pressure gauge 32, as previously discussed in FIG. 1, to provide a reading in psig of the discharged water or mixture pressure. The inclusion of the pressure gauge 32 is not mandatory, but in the preferred embodiment the gauge 32 conveniently provides the user with the measured pressure of the water or mixture provided to the nozzle assembly 24 and enables the user to precisely adjust the pressure regulating valve 30 in the manner described hereinabove to achieve the desired water or mixture pressure. The pressure gauge 32 may be located at the top of the conduit housing 20, as shown in FIG. 1, or alternatively, the pressure gauge 32 may be located in the outwardly facing side of the conduit housing 20.

Beyond the pressure gauge 32, the flow of water or mixture passes through a conduit housing outlet port 122 and a conventional male hose adaptor 124, as shown in FIGS. 1 and 2, which is affixed to the housing 20 over the outlet port 122. The hose adaptor 124 is sized so that the hose 22, as shown in FIG. 1, will fit snugly over the male end of the adaptor 124. In the preferred embodiment the hose 22 is a conventional ¼" diameter plastic hose.

The flow of water or mixture passes through the hose 22 to the conventional nozzle assembly 24, many variations of which are well known in the art. The nozzle assembly 24 of the preferred embodiment, as shown in FIG. 9, contains a normally closed (N/C) regulating valve 126 which impedes the flow of water or mixture through the nozzle assembly 24. The regulating valve 126 may be opened by the user by depressing and turning a handle 128 of the regulating valve 126 so that a conduit is opened through the regulating valve 126, allowing passage of the flow of water or mixture out a nozzle tip orifice 130. The nozzle assembly 24 also has a detachable nozzle tip 132, which may be removed from the end of the nozzle assembly 24. It is contemplated that a plurality of such nozzle tips 132 may be provided, each one with a distinguishing mark (such as a different color) so that different users may each have their own tip. As shown in FIG. 1, the non-used tips may be stored in tip nozzle recesses 134 provided in the top of the conduit housing 20.

Having now concluded a description of the construction and function of the dispenser 10, it can be seen that use of the dispenser 10 is straightforward and easily accomplished. With reference to FIG. 1, a user, desiring to use the dispenser 10 to irrigate the mouth should turn on the water, adjust the shower valves (not shown) and depress the by-pass valve 26 until the desired water temperature is obtained. The user should then adjust the flow control valve 28 to obtain the desired mixture concentration of mouthwash and water (or close the flow control valve 28 if only water is desired) and adjust the pressure of the discharged water or mixture from the nozzle assembly 24, if necessary, by turning the handle on the pressure regulating valve 30. Finally, the user should select and install the desired nozzle tip 132 on the nozzle assembly 24 and open the regulating valve 126 to receive the flow of water or mixture. When the irrigation is completed, the water valves should be turned off and the nozzle assembly 24 may be placed on a hook 136 on the conduit housing 20, as shown in FIG. I, provided for that purpose. It should be noted that once the pressure regulating valve 30 and the flow control valve 28 are adjusted to a comfortable level, they need not be readjusted to maintain that desired level.

In the preferred embodiment, the dispenser assembly 34 is sized so that the dispenser bag 76 has a capacity of about 18 fluid ounces, which has been shown to provide about a 60 minute source of mixture at a relatively moderate concentration of mouthwash. This source, depending upon usage time each day, will generally last for several days before the mouthwash in the bag must be replenished.

When the mouthwash from the dispenser bag 76 is exhausted, the dispenser bag 76 can be easily refilled by shutting off the source water and removing the dispenser assembly 34 by unscrewing it from the dispenser hub 94. The water in the dispenser assembly 34 is drained by removing the drain plug 66 from the bottom of the dispenser housing 64. The dip tube assembly 82 is removed and the dispenser bag 76, remaining in the dispenser housing 64, is refilled with mouthwash. The dip tube assembly 82 is then be reinserted into the dispenser bag 76 and the dispenser assembly 34 is screwed to the dispenser hub 94. Finally, the drain plug 66 is then inserted and tightened in the bottom of the dispenser assembly 34.

It should be readily apparent now that the preferred embodiment of the present invention relies upon the compression of the dispenser bag 76 to discharge the contents from the dispenser bag 76. The purpose of the dip tube assembly 82 is to prevent the dispenser bag 76 wall, as it collapses, from closing off the bag opening 72 before all the mouthwash has been exhausted from the dispenser bag 76. With the use of the dip tube assembly 82, the present embodiment effectively dispenses all the mouthwash from the dispenser bag 76 so that essentially no mouthwash remains when the dispenser bag 76 is emptied. It has been observed that at such times that the mouthwash in the dispenser bag 76 has been exhausted, the flow of water from the nozzle assembly 24 will "sputter", readily indicating that the mouthwash should be replenished. As a result, although the preferred embodiment for the dispenser assembly 34 has been identified as being constructed from acrylic, which is transparent, the dispenser assembly 34 could be made from an opaque material, as it is unnecessary to visually monitor the level of mouthwash remaining in the dispenser bag 76 as the dispenser 10 is in use. However, most mouthwashes are provided in a pleasing color and as such the use of a transparent dispenser assembly 34 is preferred.

Although the preferred embodiment has disclosed the use of a reusable dispenser bag 76 that remains inside the dispenser assembly 34, it is explicitly contemplated in the present invention that disposable bags of mouthwash or other hygienic fluids could be procured separately, installed, and discarded when the contents have been depleted. Of course, certain modifications might be necessary to the dispenser 10 in order to facilitate the use of disposable bags, but such modifications could be readily performed by those of skill in the art.

In addition, although the preferred embodiment has provided a dispenser for oral irrigation, the invention as disclosed and claimed would likewise cover irrigation of other body cavities besides the mouth. It is contemplated that those skilled in the art could readily modify the dispenser 10 for application of a douche or other hygienic fluid besides mouthwash, as provided in the preferred embodiment.

It will be clear that the present invention is well adapted to carry out the objects and attain the ends and advantages mentioned as well as those inherent therein. While presently preferred embodiments have been described for purposes of this disclosure, numerous changes may be made which will readily suggest themselves to those skilled in the art and which are encompassed in the spirit of the invention disclosed and as defined in the appended claims.

What is claimed is:

1. A hygiene dispenser connectable to a domestic water source, comprising:
    conduit housing means for providing a flow of water from the domestic water source; and
    dispensing means connected to the conduit housing means for selectively dispensing a hygienic fluid into the flow of water to provide a mixture of water and hygienic fluid, the dispensing means comprising:
    bag means for retaining an amount of the hygienic fluid, the bag means comprising:
        a dispenser bag having an opening and a collapsible wall, the collapsible wall having a distal end extending a selected distance from the dispenser bag opening, and
        a dispenser tube disposed within the dispenser bag, the dispenser tube having a first end proximate the distal end of the collapsible wall and a second end proximate the dispenser bag opening, and
    pressure means for exerting a pressure on the collapsible wall to selectively dispense the hygienic fluid in the bag means into the flow of water, the pressure means causing the hygienic fluid to flow through the dispenser tube by passing in a first opening in the first end of the dispenser tube and out a second opening in the second end of the dispenser tube, the dispenser tube nominally maintaining the distal end of the collapsible wall the selected distance from the dispenser bag opening to prevent the collapsible wall from blocking the dispenser bag opening and interrupting the flow of hygienic fluid from the dispenser bag.

2. The dispenser of claim 1 further comprising:
    pressure regulating means connected to the conduit housing means for regulating the pressure of the flow of water.

3. The dispenser of claim 1 further comprising:
    applicator means connected to the conduit housing means for receiving and applying the mixture from the conduit housing.

4. The dispenser of claim 1 wherein the bag means comprises a replaceable dispenser bag.

5. The dispenser of claim 1 wherein the dispensing means comprises a dispensing housing removably supported by the conduit housing means, the dispensing housing supporting the dispenser bag.

6. The hygiene dispenser of claim 1, further comprising bypass valve means for diverting water in the conduit housing means away from the dispensing means and out of the conduit housing means, the bypass valve means allowing water from the domestic water source to reach a selected temperature before the flow of water in the conduit housing means is provided to the dispensing means.

7. A dispenser connectable to a domestic water source, the dispenser comprising:
    a conduit housing having first, second, and third openings, the first opening connectable to the domestic water source to provide an inlet for a flow of water through the conduit housing;
    a dispenser assembly, connected to the second opening of the conduit housing, comprising:
        a dispenser housing;
        a dispenser bag of hygienic liquid within the dispenser housing, the bag having a collapsible wall and a bag opening in fluidic communication with the second opening of the conduit housing, the bag collapsible wall having a distal end extending a selected distance from the bag opening, the bag collapsible wall further defining a volume within the dispenser housing surrounding the bag;
        a dispenser tube disposed within the bag, the dispenser tube having a first end proximate the distal end of the bag collapsible wall and a second end proximate the bag opening; and pressure means for exerting a pressure on the bag collapsible wall by filling the volume within the dispenser housing surrounding the bag with water from the domestic water source, said pressure causing a flow of hygienic fluid to selectively dispense from the bag and mix with the flow of water through the conduit housing to provide a mixture of water and hygienic fluid; and applicator means connected to the conduit third opening for receiving and applying the mixture from the conduit housing;

wherein the flow of hygienic fluid dispenses from the bag through the dispenser tube by passing in a first opening in the first end of the dispenser tube and out a second opening in the second end of the dispenser tube, the dispenser tube nominally maintaining the distal end of the bag collapsible wall the selected distance from the bag opening, preventing the bag collapsible wall from blocking the flow of hygienic fluid from the bag.

8. The dispenser of claim 7 wherein the dispenser assembly further comprises a dispensing valve means for selectively regulating the rate of discharge of the hygienic fluid from the bag.

9. The dispenser of claim 7 wherein the applicator means further comprises:

a hose having first and second ends, the first end connectable to the third opening of the conduit housing; and a nozzle assembly connected to the hose second end.

10. The dispenser of claim 9 wherein the applicator means further comprises:

nozzle valve means connected to the nozzle assembly for regulating a flow of the mixture of water and hygienic fluid through the nozzle.

11. The dispenser of claim 9 wherein the conduit housing further comprises:

anti-siphon valve means for preventing a back flow of water from the conduit housing to the domestic water source;

bypass valve means for diverting water in the conduit housing away from the dispenser assembly and out the conduit housing, the bypass valve means allowing water from the domestic water source to reach a selected temperature before the flow of water through the conduit housing is provided to the dispenser assembly; and pressure regulation means for regulating the pressure of the flow of water through the conduit housing.

12. The dispenser of claim 8 wherein the conduit housing comprises a fourth opening and the pressure means further comprises an opening in communication with the fourth opening of the conduit housing to allow a portion of the flow of water through the conduit housing to flow into the volume within the dispenser housing surrounding the bag so as to exert the pressure upon the dispenser bag collapsible wall.

13. The dispenser of claim 12 wherein the conduit housing further comprises:

regulating means for regulating the pressure of the flow of water through the conduit housing.

14. The dispenser of claim 13 wherein the conduit housing further comprises an orifice port that reduces the pressure of the flow of water through the conduit housing so that the pressure exerted on the bag is greater than the pressure inside the bag at such times that the dispensing valve means is opened, causing the hygienic fluid contained in the bag to flow into the conduit housing.

15. The dispenser of claim 7 wherein the bag is disposable and may be replaced when essentially all hygienic fluid contained therein has been discharged.

16. The dispenser of claim 11 wherein the conduit housing further comprises a pressure gauge for measuring the pressure of the flow of water through the conduit housing.

17. A dispenser for dispensing a mixture of water and a hygienic fluid, the dispenser connectable to a domestic water source, the water source providing water at an initial pressure, the dispenser comprising:

a housing for receiving water from the domestic water source at the initial pressure and directing the water through a first channel within the housing;

a by-pass valve, connected to the first channel, for diverting the water out of the housing until such time that the water from the domestic water source reaches a desired temperature and for directing the water through a second channel within the housing after such time that the water reaches the desired temperature;

a pressure regulating valve, connected to the second channel, for reducing the pressure of the water to a selected pressure and directing the water at the selected pressure through a third channel within the housing;

a hygienic fluid dispenser assembly connected to the third channel, comprising:

a dispenser housing;

a dispenser bag disposed within the dispenser housing, the bag having a collapsible wall and a bag opening, the bag collapsible wall having a distal end extending a selected distance from the bag opening, the bag collapsible wall further defining a volume within the dispenser housing surrounding the bag;

a dispenser tube disposed within the bag, the dispenser tube having a first end proximate the distal end of the bag collapsible wall and a second end proximate the bag opening;

wherein water at the selected pressure fills the volume within the dispenser housing surrounding the bag so that hygienic fluid disposed within the bag dispenses from the bag through the dispenser tube by passing in a first opening in the first end of the dispenser tube and out a second opening in the second end of the dispenser tube, the dispenser tube nominally maintaining the distal end of the bag collapsible wall the selected distance from the bag opening, preventing the bag collapsible wall from blocking the dispensing of hygienic fluid from the bag; and wherein the dispenser further comprises:

pressure reducing means, connected to the third channel, for diverting the water through a fourth channel within the housing at a second selected pressure, the second selected pressure reduced with respect to the selected pressure;

wherein the flow of hygienic fluid from the bag mixes with the water in the fourth channel to generate the mixture of hygienic fluid and water.

18. The diverter of claim 17, further comprising applicator means, connected to the fourth channel of the housing, for receiving and applying the mixture of hygienic fluid and water.

19. The diverter of claim 17, further comprising a pressure gauge for providing an indication of the pressure of the mixture of hygienic fluid and water.

\* \* \* \* \*